United States Patent [19]

Kensey et al.

[11] Patent Number: 5,409,444
[45] Date of Patent: Apr. 25, 1995

[54] METHOD AND APPARATUS TO REDUCE INJURY TO THE VASCULAR SYSTEM

[75] Inventors: Kenneth Kensey, Chester Springs; John Nash, Dowingtown, both of Pa.

[73] Assignee: Kensey Nash Corporation, Exton, Pa.

[21] Appl. No.: 845,886

[22] Filed: Mar. 4, 1992

[51] Int. Cl.⁶ .............................................. A61M 1/12
[52] U.S. Cl. ........................................ 600/18; 600/16
[58] Field of Search .................. 600/16, 17, 18; 623/3

[56] References Cited

U.S. PATENT DOCUMENTS

| | | | |
|---|---|---|---|
| 3,592,183 | 7/1971 | Watkins | 600/18 |
| 3,818,934 | 6/1974 | Borsanyi | 600/16 |
| 4,407,271 | 10/1983 | Schiff | 600/18 |
| 4,535,757 | 8/1985 | Webster, Jr. | 600/18 |
| 4,902,273 | 2/1990 | Choy et al. | 600/18 |
| 4,957,477 | 9/1990 | Lundbäck | 600/16 |

*Primary Examiner*—William E. Kamm
*Assistant Examiner*—Kennedy J. Schaetzle
*Attorney, Agent, or Firm*—Caesar, Rivise, Bernstein, Cohen & Pokotilow, Ltd.

[57] ABSTRACT

An apparatus and method for reducing peak systolic blood pressure and the rate of change of velocity of the blood flow in a living being by passively absorbing a portion of the blood pressure during systole. The apparatus comprises an expandable/contractible chamber, e.g., a balloon, which is internally pressurized by a gas, e.g., carbon dioxide. The chamber has a surface portion which is moveable between first and second positions and vice versa when the chamber is contracted and expanded, respectively. The chamber is sufficiently small to be located at a desired situs, such as the aorta, so that the surface portion is subjected to blood pressure, whereupon it moves to the second position during systole to reduce the magnitude thereof while also reducing the rate of change of the velocity of the blood flow. The chamber expands so that the surface portion automatically returns to the first position to release an absorbed portion of the blood pressure during diastole, all the while maintaining average blood flow and pressure. A releasable anchoring mechanism is provided to hold the chamber in place within the patient's body.

60 Claims, 3 Drawing Sheets

METHOD AND APPARATUS TO REDUCE INJURY TO THE VASCULAR SYSTEM

The present invention generally relates to medical devices and more particularly to a passive device which is capable of reducing systolic blood pressure, while maintaining normal cardiac output, average blood flow and average blood pressure.

BACKGROUND OF THE INVENTION

Vascular diseases that cause clogging of arteries are the primary killer of adults in the United States. The clogging of arteries is due to an accumulation of lipids, cholesterol clots, etc., within the artery walls. The accumulation of clogging material may be accelerated by hypertension, high cholesterol, smoking and other well know risk factors. Medical researchers have therefore focused extensively on the cardiovascular system's physiology, functioning and disorders to prevent an the devastating ubiquitous disease referred to as atherosclerosis.

The study of atherosclerosis involves the study of the left ventricle and its contingent arterial system. The left ventricle is a muscular pumping chamber that pumps blood into the arterial system under high pressure. As the ventricle contracts and ejects blood into the arterial system the pressure level is dictated by the rate at which the ventricle contracts, the compliance of the vascular system, the ventricular volume, the viscosity of the blood, and the resistance of the distal capillary bed. Young persons have highly compliant vascular systems. This provides a capacitive effect that reduces peak pressure and smoothes the pulsatility of the blood flow. In adults the arteries become less compliant, thereby reducing the capacitive smoothing effect. In short, with age the blood flows at higher pressure and is more highly pulsatile.

The loss of compliance causes several related effects, namely, the peak pressure rises and the rate of change of velocity with time increases. These effects are believed to cause injury to the tissue in the artery wall, and may be the etiology of the clogging of arteries, i.e., arteriosclerosis and atherosclerosis. In particular, it is believed that the highly pulsatile flow in non-compliant vascular systems (which we call "bolus pumping" stresses the vascular system in various ways. For example, such action results in pressure induced stress and shear induced stress, with the amount of induced stress being a function of several factors, e.g., rate of change of the velocity of the blood, blood pressure, blood viscosity, red blood cell deformability. The stresses induced under bolus pumping cause the body's injury response mechanisms to react to heal the injury to maintain structural integrity, but this reaction interferes with the functionality of the artery. In short, because the artery protects itself from future injury, the artery becomes less functional.

For example, if the left ventricle ejection over stretches the aorta (e.g., as a result of elevated peak systolic pressure) injury will occur to the arterial wall. The aorta will respond in turn by thickening, hardening and becoming less compliant—medically termed "arteriosclerosis." Logically this process should first effect the region of the vascular system that is overstretched first, i.e., the aortic arch and adjacent branches due to their proximity to the left ventricle, and the peripheral vascular system (where the effects of gravity accentuates the pressure causing overstretching). These areas are where arteriosclerosis typically develops first, causing heart attacks, strokes, and necessitating the amputation of legs.

Shear stress is believed to be the underlying cause of clogging of the arteries—medically termed "atherosclerosis." In this regard bolus pumping with its highly pulsatile flow (which we call "bolus flow") is believed to induce injury to the intima. In particular, we believe that bolus flow induces injury at high shear areas within the artery, e.g., bifurcations, from friction, and induces injury at low shear areas within the artery from oscillatory fatigue. As a result the intima responds to these injuries by thickening and hardening, e.g., callus (commonly called plaque) develops, thereby resulting in arterial clogging or atherosclerosis.

All of the above described stress-induced effects are progressive and irreversible, unless some attempt is made to mechanically and/or pharmacologically correct the pressure/flow/time characteristics of the bolus flow, i.e., the pathology-inducing pulsatile flow must be eliminated or reduced.

It is recognized that the use of certain drugs or pharmaceutical, e.g., calcium channel blockers, beta blockers, etc., can modify the ejection characteristic of the left ventricle. However, such action commonly results in decreased cardiac output and significant clinical side effects.

No mechanical devices have been provided or proposed heretofore for correcting the injury producing pressure/flow/time characteristics of left ventricular ejection. Various devices, however, have been described in the patent literature for assisting cardiac output. For example, numerous types of active, intra-aortic balloon devices have been developed to assist the failing heart in pumping blood. Examples of such devices are disclosed in U.S. Pat. Nos. 3,504,662 (Jones); 3,585,983 (Kantrowitz); 3,692,018 (Goetz et al.); 3,769,960 (Robinson); 4,051,840 (Kantrowitz et al.); 4,685,446 (Choy); 4,741,328 (Gabbay); 4,861,330 (Voss); 4,902,272 (Milder et al.); 4,931,036 (Kanai et al.); and 4,994,018 (Saper).

A need thus exists for a methodology and means for correcting the injurious pressure/flow/time characteristics of the bolus flow.

OBJECTS OF THE INVENTION

Accordingly, it is a general object of this invention to provide a device and method which overcomes the disadvantages of the prior art.

It is another object of this invention to provide apparatus and a method of use for reducing systolic pressure.

It is another object of this invention to provide apparatus and a method of use for reducing the rate of change of the velocity of blood flow from the left ventricle.

It is another object of this invention to provide apparatus and a method of use for reducing the shear stress on the intima.

It is another object of this invention to provide apparatus and a method of use for reducing oscillatory shear stress on the intima.

It is another object of this invention to provide apparatus and a method of use for reducing the work load on the heart.

It is another object of this invention to provide apparatus an a method of use for reducing the work load on the heart without reducing cardiac output.

It is another object of this invention to provide apparatus and a method of use for providing compliance in a non-compliant or reduced compliance vascular system.

It is another object of this invention to provide an apparatus and a method of reducing vascular injury and thereby result in a reduction in vascular disease, such as arteriosclerosis and atherosclerosis.

SUMMARY OF THE INVENTION

These and other objects of this invention are achieved by providing an apparatus and method for reducing peak systolic blood pressure and/or the rate of change of the velocity of blood flow in a living being.

The apparatus is passive and implantable and comprises an member having a surface portion which is moveable between a first position and a second position, and vice versa. The member is sufficiently small to be located at a desired situs, such as the aorta, within the body of the being so that the surface portion is subjected to the being's blood pressure, whereupon during systole the surface portion moves from the first position to the second position to reduce the magnitude of the systolic pressure.

In accordance with a preferred embodiment the member comprises a chamber, e.g., a balloon, which is arranged to be expanded and contracted. The chamber is provided with a gas, e.g, carbon dioxide, to load the surface portion to a predetermined pressure. When the member is so located it is contracted by the blood pressure during systole so that its surface portion is moved from the first position to the second position. The movement of the surface portion of the contracting chamber effects the reduction of the magnitude of the systolic blood pressure and also reduces the rate of change of the velocity of the blood flow. During diastole the chamber automatically expands to return its surface portion to the first position. Notwithstanding the reduction in systolic pressure, normal cardiac output, average blood flow and average blood pressure is maintained.

The reduction in the systolic blood pressure and/or the rate of change of velocity of the blood flow is believed to be advantageous for various reasons. For example, such action is believed to result in the reduction in the incidence of vascular injury that leads to arteriosclerosis and atherosclerosis. Moreover the reduction in systolic blood pressure and/or rate of changes of blood velocity is believed to result in decreasing the workload of the heart (left ventricle), without a concomitant reduction in cardiac output.

DESCRIPTION OF THE DRAWING

Other objects and many attendant features of this invention will become readily appreciated as the same becomes better understood by reference to the following detailed description when considered in connection with the accompanying drawing wherein.

DETAILED DESCRIPTION OF THE PREFERRED EMBODIMENT

Figures 1, 2, 3, 6:
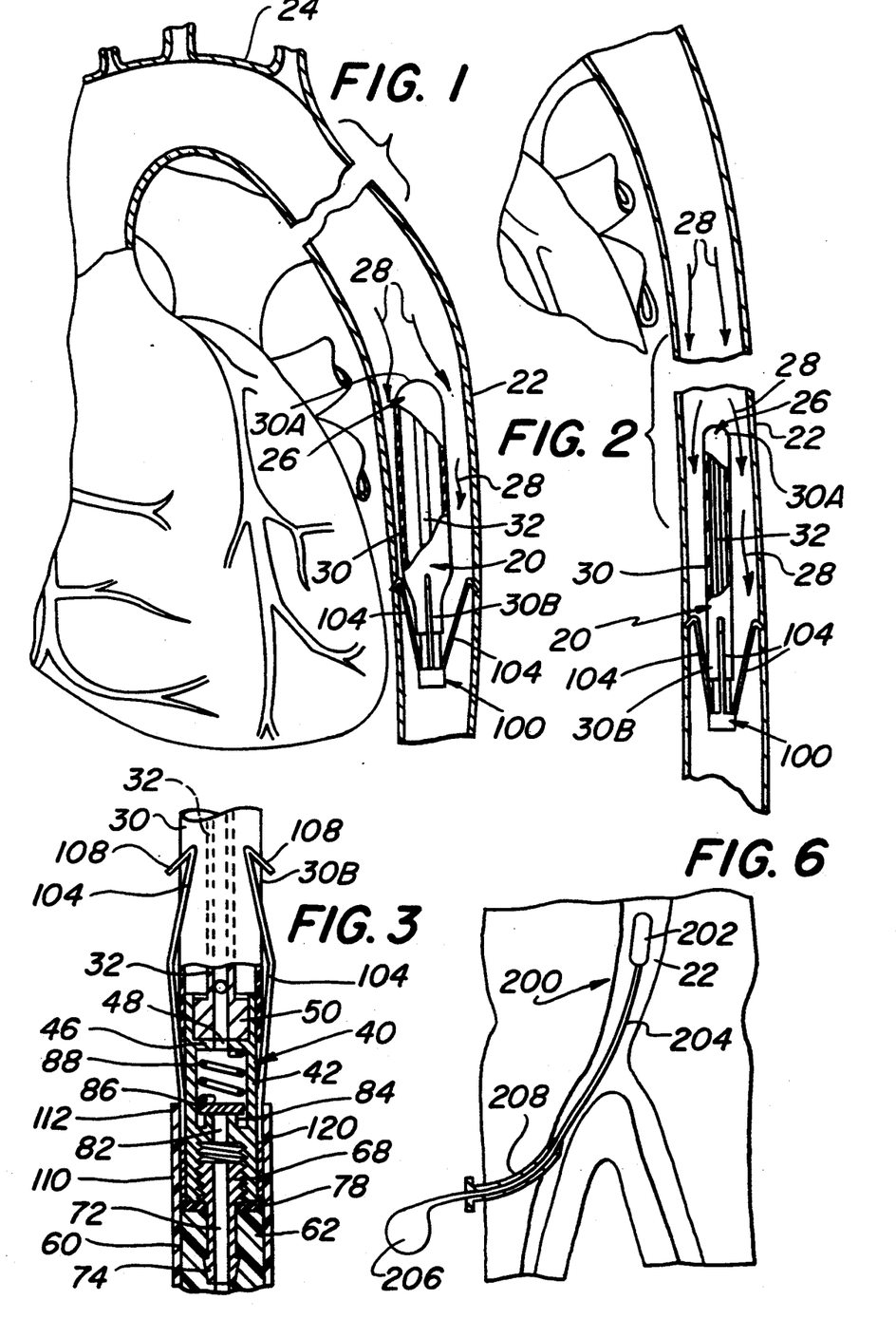
FIG. 1 is a front elevational view, partially in section, of a portion of the heart and a portion aorta of a human being showing the device of the present invention in its inflated or expanded condition during diastole.
FIG. 2 is a view similar to FIG. 1 but showing the device in its deflated or contracted condition during systole.
FIG. 3 an enlarged sectional view of a portion the device shown in FIGS. 1 and 2.
FIG. 6 is a plan view of a second embodiment of the device of the present invention shown located within the aorta of a human being.

Referring now to various figures of the drawings where like reference numerals refer to like parts, there is shown at 20 in FIG. 1, a device constructed in accordance with this invention. The device 20 is arranged to be located within the body of a living being so that it is subjected to the being's blood pressure. In the preferred embodiment the device 20 is arranged to be located within aorta 22 between the aortic arch 24 and the junction of the common iliac arteries (not shown). The device is preferably inserted into the aorta via a percutaneous incision or puncture. For example, it is contemplated that the device 20 be located on the distal end of a catheter (to be described later) which is introduced through a percutaneous incision or puncture in the femoral artery and threaded up to the desired location in the aorta to position the device therein. Once positioned the device 20 is arranged to be anchored in position by means (also to be described later) and the catheter disconnected and removed to leave the device in place for operation.

Figure 5:
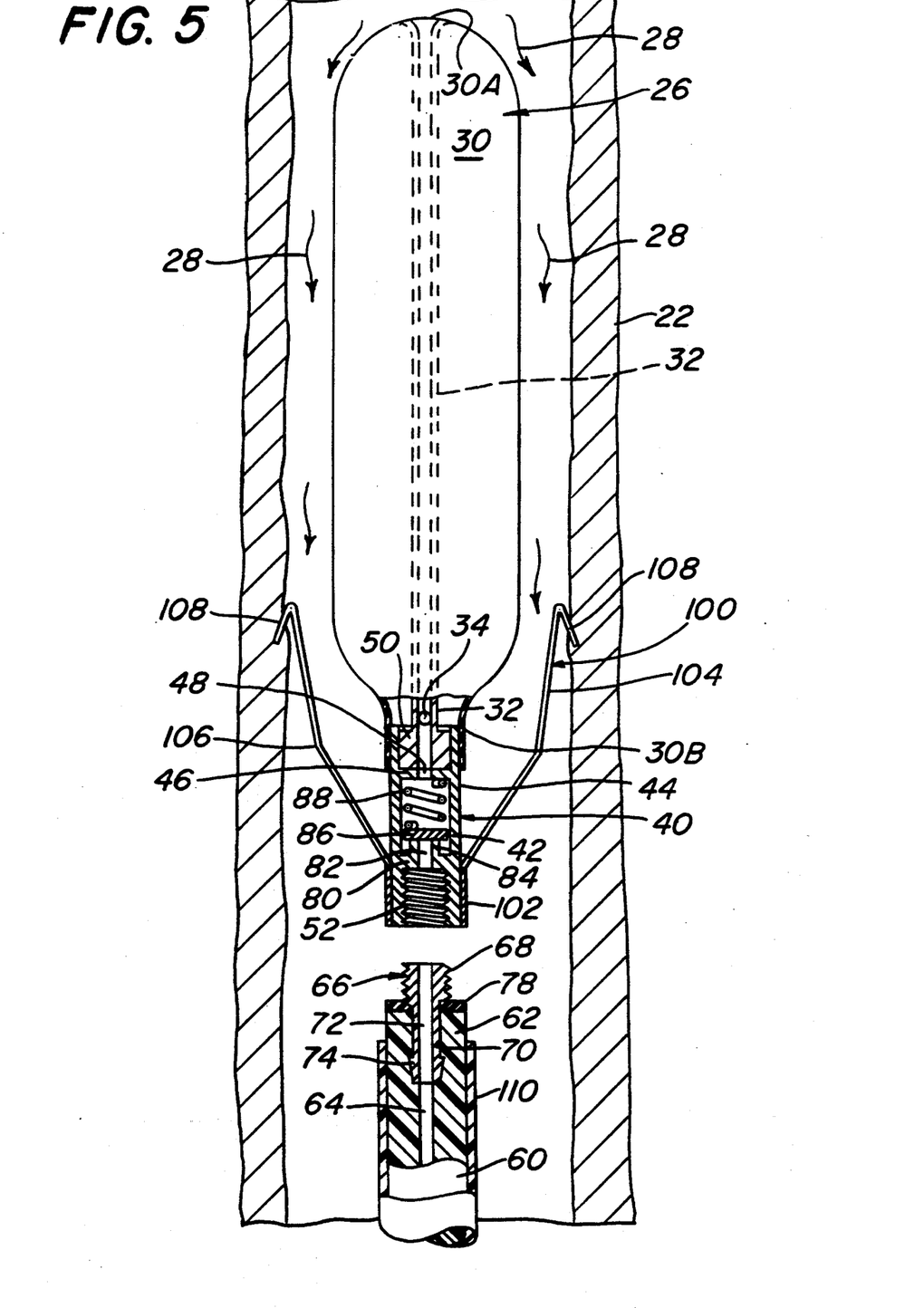
FIG. 5 is an enlarged front elevational view, partially in section, of the device and the associated portion of the aorta after the placement and inflation of the device, and showing its condition during diastole.

The device 20 is a passive member in the form of a chamber 26 which is arranged to collapse and expand in response to variations in the pressure of the blood flowing thereby. The flow of blood is denoted by the arrows bearing the reference numbers 28. In the preferred embodiment the chamber 26 comprises an elongated balloon 30 formed of a flexible, biocompatible material, e.g., a material selected from the group consisting of polyurethane and latex. The balloon 30 is arranged to be filled with a biocompatible gas, e.g, carbon dioxide, to some predetermined internal pressure, e.g., 80–120 mm Hg. The balloon is sized so that when it is inflated to the predetermined pressure it will take up a substantial volume of space within the artery during diastole, as shown in FIGS. 1 and 5. Inasmuch the balloon 30 is formed of a flexible material and its internal gas is compressible, during systole the systolic blood pressure will cause the balloon to contract to a contracted state like that shown in FIG. 2, whereupon the volume which it takes up within the aorta will be reduced. This contracting action has the effect of absorbing or reducing the systolic pressure and also reducing the rate of change, e.g., acceleration, of blood flow.

During diastole the reduced diastolic pressure enables the gas within the balloon to expand to cause the balloon to assume its expanded state again, thereby releasing the absorbed portion of the systolic blood pressure. Thus, the repeated contracting and expanding action of the balloon reduces the difference between peak systolic pressure and diastolic pressure, all the while maintaining average blood pressure and blood flow. In addition it is believed that the cardiac workload will be reduced without a concomitant reduction in cardiac output. Moreover, the reduction of peak systolic pressure should result in a reduction in pressure-induced-injury, e.g., arteriosclerosis, while the reduction the rate of change of blood flow should result in a reduction of the shear stress on the intima, thereby reducing the incidence of shear stress-induced-injury, e.g, atherosclerosis.

The volumetric capacity of the balloon 30 is selected so that it can collapse to absorb enough of the ventricular ejection volume to significantly lessen peak systolic pressure. Since the heart of an adult typically ejects 2–6 liters per minute, the ejection volume per contraction of the heart will be between 25–100 ml (assuming a pulse rate range of 60–80 beats per minute). Adult patients for whom the subject invention may prove beneficial are typically unfit and hence would have an ejection volume per cycle at the low end of the range, e.g., 20–30 ml per cycle. In order to meaningfully reduce the systolic pressure of such persons using devices in which the collapsible chamber is composed of a balloon like that described heretofore it is contemplated that the balloon 30 should have a volumetric capacity so that when it is in expanded state during diastole it displaces at least 5 ml of blood volume within the artery (for pediatric applications the volumetric capacity may be less, e.g., 1 or 2 ml.) Accordingly, when the balloon is contracted by the systolic pressure it can effect a significant reduction in systolic pressure. Larger capacity balloons can be expected to provide even greater reductions in the systolic pressure. Thus, it is contemplated that the chamber can be made significantly greater in volume, e.g, 50 ml, so long as it is suitable for disposition within the vascular system, e.g, the aorta.

As mentioned earlier the material making up the balloon is flexible. Preferably such is non-elastic so that it will not stretch during its expansion cycle, which stretching over a sustained period of time could result in material fatigue and rupture. If the material making up the balloon is elastic, the balloon should be sized and pressurized so that when the balloon is in its expanded state during systole it will not be stretched to a substantial degree.

As can be seen clearly in FIGS. 1–3 and 5 the balloon 30 includes a relatively rigid mandrel 32 which extends longitudinally down the length of the balloon from its distal end 30A to its proximal end 30B. The mandrel is secured to the balloon distal end of the balloon and to a connector (to be described later) at the proximal end of the balloon to hold the balloon in an elongated configuration generally parallel to the longitudinal axis of the portion of the blood vessel in which it is located. The mandrel also serves to prevent the longitudinal collapse, e.g., mushrooming or flattening, of the distal end 30 of the balloon which could result from the onrushing blood 28.

As can be seen clearly in FIG. 5 the mandrel 32 is a hollow tubular member having at least one port or orifice 34 communicating with the interior of the balloon through which the gas is introduced into the balloon to inflate it. In accordance with a preferred embodiment the balloon is inflated after it is in place within the blood vessel, e.g, aorta. By so doing the uninflated size of the balloon can be sufficiently small that it can be introduced into the vessel via a percutaneous incision or puncture, such as that described heretofore.

Figure 4:
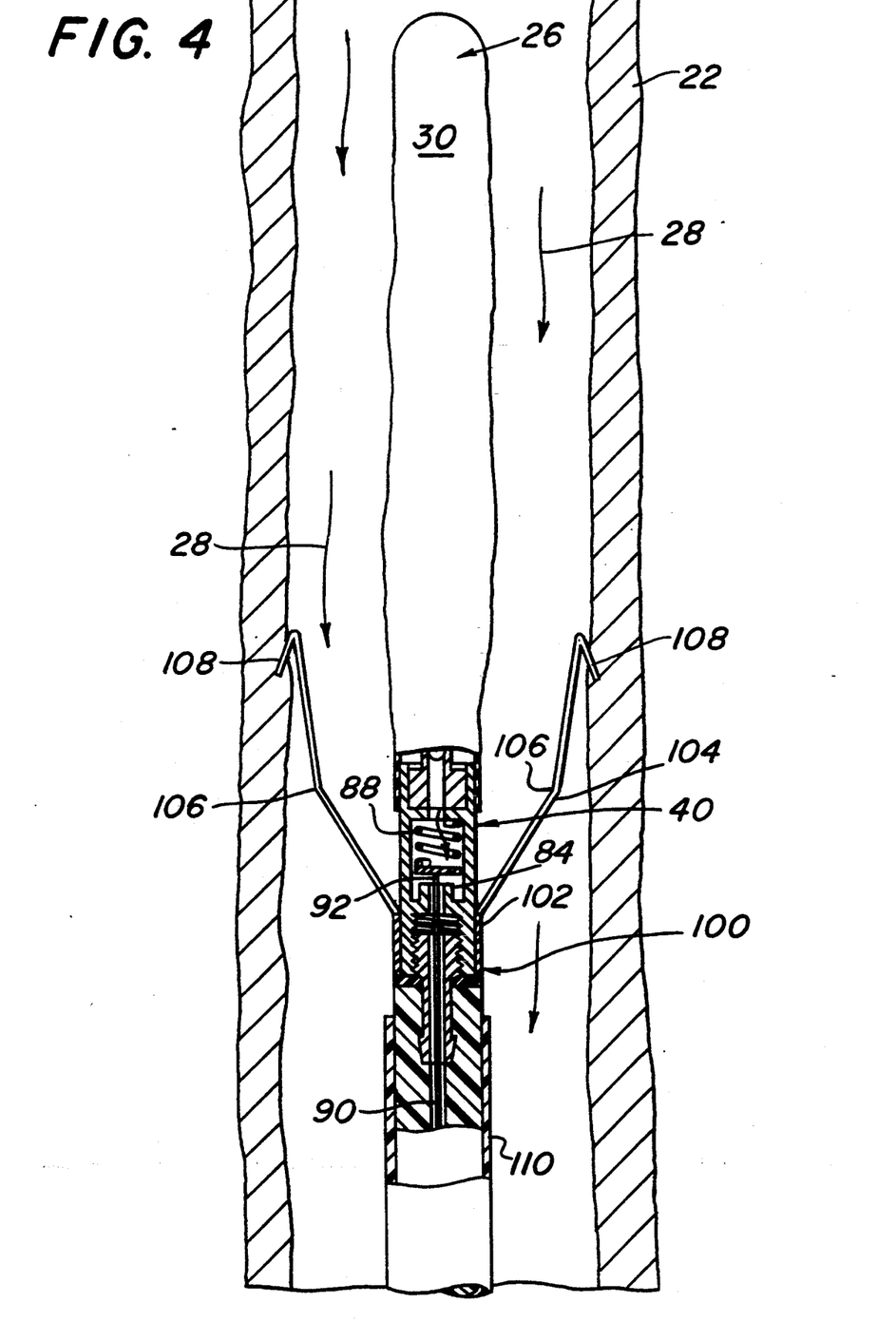
FIG. 4 is an enlarged front elevational view, partially in section, of the device and the associated portion of the aorta during the placement of the device therein and before inflation thereof.

The means for effecting the location, positioning and inflation of the balloon 30 will now be described with reference to FIGS. 3–5. Thus, as can be seen therein the proximal end 30B of the balloon terminates in a connector/valve assembly 40. That assembly basically comprises a tubular member 42 having an outer surface 44 to which the periphery of the distal end of the balloon is secured. The member 42 includes a first intermediate wall 46 located adjacent the distal end of the member 42. The wall 46 extends transversely of the longitudinal axis of the member 42 and includes a central opening or hole 48 therein. The proximal end 50 of the mandrel 32 is in the form of an annular flange which is disposed on the distal side of the wall 46 so that the central hole 48 is in communication with the interior of the mandrel 32 and its port 34.

The proximal end of the tubular member 42 includes an internally threaded bore 52. The bore 52 is arranged to receive the distal end of a catheter 60. The catheter 60 basically comprises an elongated tube or jacket 62 having a lumen 64 extending therethrough. A connector 66 is located at the distal end of the jacket. The connector includes an externally threaded distally projecting tubular section 68 and a proximally projecting tubular section 70. A central passageway 72 extends through the connector between its sections 68 and 70. The section 70 has a locking ledge 74 extending about its periphery for location within the distal end of the lumen 64 to fixedly secure the connector 66 in place on the catheter. The threaded section 66 of the connector is arranged to be threadedly secured within the threaded bore 52 to releasably secure the balloon onto the distal end of the catheter 60. A resilient disk-like gasket 78 is disposed on the end of the jacket about the externally threaded section 68.

The tubular member 42 includes a second intermediate wall 80 located adjacent the proximal end of the member 42. The wall 80 extends transversely of the longitudinal axis of the member 42 and includes a central opening or hole 82 about which is located an upstanding valve seat 84. The hole 82 communicates with the lumen 64 in the catheter 60 when the balloon is secured thereto.

The space within the tubular member 42 between the intermediate walls 46 and 80 defines a valve chamber in which a disk-like valve element 86 is located. The valve element 86 is disposed on the valve seat 84. A helical compression spring 88 is located within the valve chamber interposed between the valve element 86 and the intermediate wall 46 to bias the valve element into engagement with the valve seat and thereby close the opening 82. Thus, the valve made up of the foregoing elements is in a normally closed state isolating the interior of the balloon from the ambient surroundings.

The gas for inflating the balloon 30 is introduced through the valve. In order to open the normally closed valve, an elongated wire 90 (FIG. 4) is passed through the lumen 64 and the passageway in the connector 66 so that its distal end 92 passes into the tubular member 42 and its opening 82 to lift the valve element 86 off of the valve seat 84 against the bias of the spring 88 as shown therein. The gas can then be passed from some external source (not shown) through the catheter's lumen, the open valve, and the hole 48 into the interior of the mandrel 32, from which it flows through the port 34 into the balloon. Thus, the balloon can be readily inflated to the desired pressure. Once the balloon is inflated to the desired pressure, the wire 90 is retracted so that the biasing spring causes the valve element to move back into sealing engagement on the valve seat, thereby closing the valve and preventing the gas within the balloon from gaining egress therefrom. The balloon is then disconnected from the catheter (a process to be described later).

As mentioned earlier the balloon includes means for anchoring or fixing it at the desired location within the being's vascular system. Such means basically comprises a releasably securable anchoring assembly 100. The assembly basically comprises a sleeve 102 disposed over and secured to the outer surface of the tubular member 42 adjacent its proximal end. A plurality of flexible tines 104 project outward at an acute angle from the sleeve. Each tine includes a jog 106 at an intermediate point. The distal or free end 108 of each tine 104 is in the form of a hook. The tines are formed of a resilient material so that when unconstrained they assume the outward orientation shown in FIG. 4. By pulling on the catheter in the proximal direction the free ends 108 of the hooks engage, e.g., penetrate, the tissue making up the artery wall to hold the balloon 30 at a fixed position generally centered therein.

The tines are arranged to be held within a constrained or retracted position when the balloon is introduced into the body of the being so that they do not impede the positioning procedure. Thus, when the balloon is being inserted to the desired situs an elongated sleeve 110 is provided about the jacket of the catheter. At this time the sleeve 110 is located in the position shown in FIG. 3, whereupon its distal end 112 overlies the base of the tines 104. This action has the effect of flexing the tines inward toward the central longitudinal axis of the device, whereupon the free ends of the tines do not extend appreciably beyond the periphery of the balloon. Thus, the balloon can be readily threaded through the arterial system to its desired situs. Once in the desired position the sleeve 110 is slid longitudinally with respect to the catheter in a proximal direction, whereupon its distal end 112 uncovers the base of the tines so that the are released to flex outward to the position shown in FIG. 4. The catheter, with the balloon attached thereto, is then pulled in the proximal direction to cause the hooks at the free ends of the tines to engage the arterial wall as described earlier. This action anchors the balloon in place.

Once the balloon is anchored it is inflated as described earlier. After the balloon is inflated the catheter is ready to be removed. To achieve that end the catheter is rotated about its longitudinal axis to unthread its connector 66 from the balloon's tubular member 42. Once that has been accomplished the catheter can be withdrawn and removed from the body of the patient, leaving the balloon in place.

In accordance with a preferred embodiment of this invention the balloon and the catheter each include radiopaque means (not shown) to enable them to be imaged radiographically, thereby facilitating their use.

The balloon of the subject invention can be left in place within the body of the patient permanently or for a indefinite or definite period of time. In the later cases the balloon can be readily removed by use of the catheter 60. To that end the catheter 60 is introduced, e.g., percutaneously, until its distal end is adjacent the tubular member 42 of the balloon. The catheter's connector 66 can then be threadedly engaged in the bore of the member 42 by rotating the catheter about its longitudinal axis. The balloon is then ready to be deflated. This is accomplished by introducing the wire 90 through the catheter's lumen to unseat the valve element. The balloon can then be evacuated via the lumen in the catheter. Once that has been accomplished the catheter is then moved slightly in the distal direction to free the hooks of the tines from engagement with the arterial tissue. Then the sleeve 110 is slid in a distal direction down the catheter jacket until its distal end covers the base of the tines, whereupon the tines are flexed back to their retracted position like that shown in FIG. 3. The balloon can then be withdrawn from the body of the being by retracting the catheter.

Because of the limited range of pressures to which the balloon 20 will be exposed during operation, a balloon of sufficient volumetric capacity to significantly reduce systolic pressure will nevertheless have a rather sizable collapsed (contracted) volume. This may be deemed undesirable. Thus, it is contemplated to utilize a static (fixed) size chamber in combination with an expandable/contractible balloon located within a blood vessel, so that one may reduce the size of the expandable/contractible balloon and still effect the same systolic pressure reduction as can achieved by a larger size expandable/contractible balloon.

Thus, in FIG. 6 there is shown an alternative embodiment of the device of this invention. That device is designated by the reference numeral 200 and basically comprises an expandable/collapsible balloon 202 located in the aorta coupled, via a flexible conduit 204, to a static (fixed size) chamber 206 located elsewhere, e.g., located exteriorly of the patient's body. The conduit 204 passes through any type of introducer or coupling 208 extending into the patient's body, e.g., into the femoral artery. Alternatively, the static chamber 206 may be implanted at any suitable location in the being's body.

In any case the balloon portion 202 of the apparatus 200 is of similar construction to the balloon 30 described heretofore except for the lack of a valve and its associated components. Instead the tubular member 42 of balloon portion 202 merely includes some means to enable it to be secured to the distal end of the conduit 204 so that there is a fluid passageway between the balloon portion 202 and the fixed size chamber 206. The balloon portion 202 may be held in position in the same manner and by the same means as used with balloon 30.

The balloon 202 operates in the same general manner as described heretofore with reference to balloon 30. Thus, during diastole the gas in the balloon is enabled to expand so that its wall moves to the position shown in FIGS. 1 and 5. During systole the increased pressure causes the balloon 202 to contract. Since the balloon 202 is not self contained, the gas within the balloon and within the communicating conduit 204 and the static chamber 206 is compressed by the contraction of the balloon 202. Thus, the balloon and associated conduit and chamber coact to absorb a portion of the systolic pressure.

In lieu of the static or fixed size chamber 206, a variable size chamber, located either externally or internally of the patient's body, can be used in combination with the expandable/contractible chamber (e.g., balloon 30/202) subjected to the blood pressure/flow. For example the externally located chamber 206 shown in FIG. 6 (or any internally located chamber coupled to the expandable/collapsible balloon) can be made in any convenient manner so that its size or volumetric capacity is variable. By so doing one can readily establish or adjust the internal pressure level (and thus the collapse pressure) within the associated expandable/contractible balloon. This feature may prove advantageous in cases where heart bypass has been completed and where the patient needs his/her blood pressure relieved during the repair period. Moreover, with such an arrangement one could increase the pressure gradually to test out the heart.

As should be appreciated from the foregoing the device of this invention, e.g., a partially inflated balloon in the aorta, acts as a damper to mechanically restore vascular system compliance, it reduces peak systolic pressure, and also reduces the rate of change, e.g., acceleration and/or deceleration, of the blood flow. These factors are believed to result in the prevention or minimization of vascular-injury-induced disease. In addition to the primary tasks of this invention, its use should result in a reduction in the cardiac workload, without a concomitant reduction in cardiac output. Thus, the subject invention should be useful for passively offloading the heart in cases of impending heart failure, such as post myocardial infarction or post-bypass surgery.

Without further elaboration the foregoing will so fully illustrate our invention that others may, by applying current or future knowledge, adapt the same for use under various conditions of service.

We claim:

1. A method of reducing the magnitude of systolic blood pressure of a living being by the use of passive pressure absorption means comprising a first chamber having a gas therein pressurizing said chamber to a predetermined internal pressure, said chamber being expandable to an expanded state and contractible to a contracted state, and vice versa, said method comprising locating said first chamber within the body of said being at a desired situs to subject said first chamber to the being's blood pressure, whereupon during systole said first chamber contracts from said expanded state to said contracted state to thereby reduce the magnitude of the systolic pressure, said first chamber expanding to said expanded stated during diastole, whereupon said first chamber releases an absorbed portion of said systolic blood pressure.

2. The method of claim 1 wherein said gas is introduced into said first chamber after said passive pressure absorption means is located within the body of said being.

3. The method of claim 1 wherein said first portion is located within the aorta.

4. The method of claim 1 additionally comprising providing a second chamber in fluid communication with said first chamber.

5. The method of claim 4 wherein said second chamber is of a predetermined volumetric capacity.

6. The method of claim 5 wherein said predetermined volumetric capacity is fixed.

7. The method of claim 5 wherein said predetermined volumetric capacity is variable.

8. The method of claim 4 wherein said second chamber is located remote from said first chamber.

9. The method of claim 8 wherein said second chamber is located outside of the body of said being.

10. The method of claim 8 wherein said second chamber is located within the body of said being.

11. The method of claim 1 wherein a portion of said apparatus is made radiographic to facilitate the location of said first portion at said situs within the body of said being.

12. The method of claim 1 wherein said first chamber is located within said vascular system and wherein said method additionally comprises providing a second chamber in fluid communication with said first chamber, said second chamber being located externally of said vascular system.

13. The method of claim 12 wherein said second chamber is located outside the body of said being.

14. A method of reducing the magnitude of systolic blood pressure of a living being by the use of passive pressure absorption means comprising a first chamber and a second chamber in fluid communication with each other, said first chamber having a gas therein and being expandable to an expanded state and contractible to a contracted state, and vice versa, said method comprising locating said second chamber outside the body of said being, locating said first chamber within the body of said being at a desired situs to subject said first chamber to the being's blood pressure, whereupon during systole said first chamber contracts from said expanded state to said contracted state to thereby reduce the magnitude of the systolic pressure, said first chamber expanding to said expanded stated during diastole, whereupon said chamber releases an absorbed portion of said systolic blood pressure.

15. A method of reducing the magnitude of the change in velocity of the flow of blood in a living being by the use of passive means comprising a first chamber having a gas therein pressurizing said chamber to a predetermined internal pressure, said chamber being expandable to an expanded state and contractible to a contracted state, and vice versa, said method comprising locating said first chamber within the body of said being at a desired situs to subject said first chamber to the being's blood flow, whereupon during systole said first chamber contracts from said expanded state to said contracted state to thereby reduce the magnitude of the change in velocity of said blood, said first chamber expanding to said expanded state during diastole.

16. The method of claim 15 wherein said gas is introduced into said first chamber after said passive means is located within the body of said being.

17. The method of claim 15 wherein said first chamber is located within the aorta.

18. The method of claim 15 additionally comprising providing a second chamber in fluid communication with said first chamber.

19. The method of claim 18 wherein said second chamber is of a predetermined volumetric capacity.

20. The method of claim 19 wherein said predetermined volumetric capacity is fixed.

21. The method of claim 19 wherein said predetermined volumetric capacity is variable.

22. The method of claim 18 wherein said second chamber is located remote from said first chamber.

23. The method of claim 22 wherein said second chamber is located within the body of said being.

24. The method of claim 15 wherein a portion of said apparatus is made radiographic to facilitate the location of said first portion at said situs within the body of said being.

25. The method of claim 15 wherein said first chamber is located within said vascular system and wherein said method additionally comprises providing a second chamber in fluid communication with said first chamber, said second chamber being located externally of said vascular system.

26. The method of claim 25 wherein said second chamber is located outside the body of said being.

27. A method of reducing the magnitude of the change in velocity of the flow of blood in a living being by the use of passive means comprising a first chamber and a second chamber in fluid communication with each other, said first chamber having a gas therein and being expandable to an expanded state and contractible to a contracted state, and vice versa, said method comprising locating said second chamber outside the body of said being, locating said first chamber within the body of said being at a desired situs to subject said first chamber to the being's blood flow, whereupon during systole said first chamber contracts from said expanded state to said contracted state to thereby reduce the magnitude of the change in velocity of said blood, said first chamber expanding to said expanded stated during diastole.

28. An apparatus for reducing the magnitude of systolic blood pressure in the cardiovascular system of a living being, said apparatus comprising passive pressure absorption means, said passive pressure absorption means comprising a first chamber means having a gas therein which is pressurized to a predetermined internal pressure, said chamber means for expansion and contraction when subjected to the being's blood pressure, said first chamber means being arranged to be located at a desired situs within the body of said being so that said first chamber is subjected to the being's blood pressure, whereupon the first chamber means contracts to a contracted state by said blood pressure during systole to reduce the magnitude of systolic pressure, and expands to an expanded state during diastole.

29. The apparatus of claim 28 wherein said first chamber means is arranged to automatically return to said expanded state to release an absorbed portion of the blood pressure during diastole.

30. The apparatus of claim 28 wherein said first chamber means comprises an inflatable balloon.

31. The apparatus of claim 30 wherein the material forming said balloon is inextensible.

32. The apparatus of claim 30 additionally comprising a second chamber means in fluid communication with said first chamber means.

33. The apparatus of claim 32 wherein said second chamber means is of a predetermined volumetric capacity.

34. The apparatus of claim 33 wherein said second chamber means is of a variable volumetric capacity.

35. The apparatus of claim 33 wherein said second chamber means is of a fixed volumetric capacity.

36. The apparatus of claim 28 additionally comprising a second chamber means in fluid communication with said first chamber means.

37. The apparatus of claim 36 wherein said second chamber means is of a predetermined volumetric capacity.

38. The apparatus of claim 37 wherein said second chamber means is of a fixed volumetric capacity.

39. The apparatus of claim 38 wherein said second chamber means is of a variable volumetric capacity.

40. The apparatus of claim 39 wherein said second chamber is arranged to be located outside the body of said being.

41. The apparatus of claim 38 wherein said second chamber is arranged to be located outside the body of said being.

42. The apparatus of claim 28 additionally comprising anchoring means for anchoring said first chamber means at said situs.

43. The apparatus of claim 42 wherein said anchoring means is releasably securable to said situs.

44. The apparatus of claim 28 wherein said first chamber means is configured for location within said vascular system and wherein said passive pressure absorption means additionally comprises a second chamber means in fluid communication with said first chamber means, said second chamber means being arranged for location externally of said vascular system.

45. The apparatus of claim 44 wherein said second chamber means is arranged for location outside the body of said being.

46. An apparatus for reducing the magnitude of the change in velocity of blood flow in a living being, said apparatus comprising first chamber means for expansion and contraction when subjected to said being's blood pressure and having a gas therein which is pressurized to a predetermined internal pressure, said first chamber means being arranged to be located at a desired situs within the body of said being so that said first chamber means is subjected to the being's blood flow, whereupon said first chamber means contracts to a contracted state by said blood flow during systole to thereby reduce the magnitude of the change in its velocity, said first chamber means expanding to an expanded stated during diastole.

47. The apparatus of claim 46 wherein said first chamber means comprises an inflatable balloon, 48. The apparatus of claim 47 wherein the material forming said balloon is inextensible.

49. The apparatus of claim 46 additionally comprising a second chamber means in fluid communication with said first chamber, 50. The apparatus of claim 49 wherein said second chamber means is of a predetermined volumetric capacity, 51. The apparatus of claim 50 wherein said second chamber means is of a fixed volumetric capacity, 52. The apparatus of claim 51 wherein said second chamber is arranged to be located outside the body of said being.

53. The apparatus of claim 50 wherein said second chamber means is of a variable volumetric capacity, 54. The apparatus of claim 53 wherein said second chamber is arranged to be located outside the body of said being.

55. The apparatus of claim 46 additionally comprising anchoring means for anchoring said first chamber means at said situs, 56. The apparatus of claim 55 wherein said anchoring means is releasably securable to said situs.

57. The apparatus of claim 46 wherein said first chamber means is configured for location within said vascular system and wherein said passive pressure absorption means additionally comprises a second chamber means in fluid communication with said first chamber means, said second chamber being arranged for location externally of said vascular system.

58. The apparatus of claim 57 wherein said second chamber means is arranged for location outside the body of said being.

59. An apparatus for reducing the magnitude of systolic blood pressure in the cardiovascular system of a living being, said apparatus comprising passive pressure absorption means, said passive pressure absorption means comprising a first chamber means and a second chamber means in fluid communication with each other, said second chamber means being arranged to be located outside the body of said being, said first chamber means for expansion and contraction when subjected to the being's blood pressure and having a gas therein, said first chamber means being arranged to be located at a desired situs within the body of said being so that said first chamber means is subjected to the being's blood pressure, whereupon the first chamber means contracts to a contracted state by said blood pressure during systole to reduce the magnitude of systolic pressure and expands to an expanded state during diastole.

60. An apparatus for reducing the magnitude of the change in velocity of blood flow in a living being, said apparatus comprising a first chamber means and a second chamber means in fluid communication with each other, said second chamber means being arranged for location outside the body of said being, said first chamber means for expansion and contraction when subjected to said being's blood pressure and having a gas therein, said first chamber means being arranged for location at a desired situs within the body of said being so that said first chamber means is subjected to the being's blood flow, whereupon the first chamber means contracts to a contracted state by said blood flow during systole to thereby reduce the magnitude of the change in its velocity and expands to an expanded state during diastole.

* * * * *